US010940271B2

(12) United States Patent
Holmqvist (10) Patent No.: US 10,940,271 B2
(45) Date of Patent: Mar. 9, 2021

(54) PLUNGER SLACK SYRINGE

(71) Applicant: GALDERMA S.A., Cham (CH)

(72) Inventor: Anders Holmqvist, Värmdö (SE)

(73) Assignee: Galderma Holding SA, La Tour-de-Peilz (CH)

( * ) Notice: Subject to any disclaimer, the term of this patent is extended or adjusted under 35 U.S.C. 154(b) by 190 days.

(21) Appl. No.: 16/087,850

(22) PCT Filed: Mar. 31, 2017

(86) PCT No.: PCT/EP2017/057725
§ 371 (c)(1),
(2) Date: Sep. 24, 2018

(87) PCT Pub. No.: WO2017/167979
PCT Pub. Date: Oct. 5, 2017

(65) Prior Publication Data
US 2020/0001013 A1   Jan. 2, 2020

(30) Foreign Application Priority Data

Mar. 31, 2016  (EP) .................................... 16163370

(51) Int. Cl.
*A61M 5/315* (2006.01)
*A61M 5/31* (2006.01)

(52) U.S. Cl.
CPC ........ *A61M 5/3157* (2013.01); *A61M 5/3137* (2013.01); *A61M 5/31515* (2013.01);
(Continued)

(58) Field of Classification Search
CPC ............ A61M 5/3157; A61M 5/31515; A61M 5/31511; A61M 5/31573; A61M 5/32;
(Continued)

(56) References Cited

U.S. PATENT DOCUMENTS

2011/0306947 A1* 12/2011 Boyd ................ A61M 5/31555
604/506
2012/0010575 A1*  1/2012 Jones ................ A61M 5/31555
604/211
2012/0022464 A1*  1/2012 Zivkovic ............. A61M 5/3234
604/198

FOREIGN PATENT DOCUMENTS

EP       2698179 A1   2/2014
WO    2008057976 A2   5/2008
(Continued)

OTHER PUBLICATIONS

V.S Bagad, Mechatronics, 2009, Technical Publications, p. 1-8. (Year: 2009).*
(Continued)

*Primary Examiner* — Kevin C Sirmons
*Assistant Examiner* — Tezita Z Watts
(74) *Attorney, Agent, or Firm* — Foley & Lardner LLP; Sunit Talapatra (57) ABSTRACT

The present specification relates to a syringe comprising a barrel, a plunger moveably arranged within the barrel and a plunger rod for driving the plunger, and a mechanism for providing feedback to a user as the plunger rod is moved relative to the barrel for driving said plunger such that feedback is given to a user as the plunger rod is moved relative to the barrel for driving the plunger. The plunger rod is arranged to drive the plunger such that a predetermined relative movement between at least a portion of the plunger rod and the plunger is allowed. The present specification further relates to a plunger assembly wherein a predetermined relative movement between at least a portion of the plunger rod and the plunger is allowed.

11 Claims, 3 Drawing Sheets

(52) U.S. Cl.
CPC . *A61M 5/31573* (2013.01); *A61M 2005/3114* (2013.01); *A61M 2005/3139* (2013.01); *A61M 2205/581* (2013.01); *A61M 2205/582* (2013.01)

(58) Field of Classification Search
CPC .......... A61M 5/20; A61M 5/00; A61M 5/178; A61M 2005/3139; A61M 2205/581; A61M 2205/582; A61M 2205/583
See application file for complete search history.

(56) References Cited

FOREIGN PATENT DOCUMENTS

| | | |
|---|---|---|
| WO | 2011123024 A1 | 10/2011 |
| WO | 2013178512 A1 | 12/2013 |
| WO | 2014139916 A1 | 9/2014 |

OTHER PUBLICATIONS

International Search Report (PCT/ISA/210) dated Jun. 16, 2017, by the European Patent Office as the International Searching Authority for International Application No. PCT/EP2017/057725.

Written Opinion (PCT/ISA/237) dated Jun. 16, 2017, by the European Patent Office as the International Searching Authority for International Application No. PCT/EP2017/057725.

* cited by examiner

PLUNGER SLACK SYRINGE

TECHNICAL FIELD

The present invention generally relates to syringes, and more particularly to a syringe that is able to provide a user with feedback during use.

TECHNICAL BACKGROUND

When a user of a medical syringe administers a substance, it is common, in particular within certain areas of treatment, to distribute the total volume carried by the syringe over an area. Some examples of such areas of treatment are dermatology, plastic surgery, cosmetic surgery, and odontology. The distribution is for instance done by inserting the needle of the syringe just beneath and approximately in parallel with the skin surface and then administering the substance while withdrawing the needle. Another way is to administer the substance at several anatomic locations within a limited area, i.e. to administer a fraction of the total volume at each location.

In these, and other, methods of distributing the substance it is an advantage if the syringe is provided with some kind of dosing aid, which aids the user in knowing how large fraction of the total volume of the substance is administered at each location or per time unit.

Known examples of dosing aids include the dosing scale traditionally provided on syringes, where known problems include difficulties for a user to see the scale during injection and mechanical and electronic injectors which however tend to be more expensive and heavier than traditional syringes.

In order to alleviate some of these drawbacks, attempts have been made to provide a syringe with user friendly means that informs and provides feedback to a user about the injected amount or an injection rate. For example, syringes comprising mechanisms wherein for example an engagement member is provided on the finger grip and/or plunger rod to engage with a structure of the plunger rod in order to provide for example audible feedback to a user corresponding to a delivered dose are known. One such an effort to provide a syringe with a dosing aid is disclosed in WO2008057976.

However, in some of the prior art solutions, there is a problem with engagement members that during aspiration or draw up of a substance will be misorientated or in some cases even biased in an opposite direction, as compared to the direction of movement when engaging the other member during injection. Such engagement members may during injection of a first dose require the plunger rod to travel much farther than initially intended for a feedback signal before the first signal is generated.

It has been shown in tests that the first dose in such prior art syringes can be up to three times larger than intended. Such overdosing is of course highly unwanted and can in certain cases have devastating effects causing e.g. unintended muscle paralysis.

SUMMARY OF THE INVENTION

Accordingly, it would be desirable to provide an improved syringe providing feedback to a user during injection corresponding to for example the amount delivered. In particular, it would be desirable to provide an increased accuracy of the delivered dosage, for example with regard to the first dose delivered after a reversal of the direction of movement. To better address one or more of these concerns a syringe as defined in the independent claim is provided. Preferred embodiments are defined in the dependent claims.

According to a first aspect of the invention a syringe comprising a barrel, a plunger assembly, which comprises a plunger moveably arranged within the barrel and a plunger rod for driving the plunger, and a mechanism for providing feedback to a user as the plunger rod is moved relative to the barrel for driving said plunger is provided. The mechanism comprises a feedback triggering portion arranged at an outer surface of the plunger rod and extending along the plunger rod, and a feedback generating element arranged at the barrel, and arranged to generate feedback by being triggered by the feedback triggering portion during movement of the plunger rod relative to the barrel. The plunger assembly comprises a first assembly part consisting of at least a part of the plunger rod, and a second assembly part consisting of at least the plunger, and a connection portion where the first and second assembly parts are connected with a play, thereby allowing a predetermined free relative movement between the first assembly part and the second assembly part within a predetermined distance d, in a longitudinal direction of the plunger rod.

According to the first aspect, the syringe provides an inventive solution to the concerns described above by means of the design incorporating a plunger and a plunger rod for driving the plunger, arranged such that a predetermined free relative movement between at least a portion of the plunger rod and the plunger is allowed. During such a relative movement, the plunger rod may for example be allowed to move while the plunger remains still. By the term free is meant that there is no resilient, spring biased, or in some other way compactable or movable element between the first and second assembly parts causing an additional force to overcome. There may still be a degree of, for instance, friction having a minor but insignificant effect on the movement.

This is particularly relevant for the relationship between the feedback provided to the user and the size of the delivered dose, and even more so for the relationship between the first dose after a reversal of the direction of movement of the plunger rod and the provision of a first feedback indication. Commonly, the feedback to the user is provided in the form of feedback indications, each feedback indication corresponding to a certain dose being delivered. The feedback indication may also be described as indicative of the plunger rod having travelled a certain distance. The dose, i.e. the amount of substance delivered, on the other hand may be described as proportional to the distance travelled by the plunger.

This is as such also true for example for the prior art solutions described above, wherein the plunger rod in some situations however is required to travel much farther than what is normally required before the first feedback indication is generated after a reversal of movement, for example due to elements comprised by a feedback generating mechanisms becoming misorientated, misaligned or the like. One example of such a reversal of movement is the reversal of movement when delivering a first dose of a substance following aspiration of the substance into the syringe. The associated problems relating to the first dose consequently being largely due to the extra travel required by the plunger rod as well as the plunger arranged on the plunger rod, are also known.

For example, the in syringe presented in WO2008057976 mentioned above the mechanism comprises an engagement member consisting of a flat member lying on top of the finger grip interacting with a grooved surface of the plunger 
rod, see e.g. FIGS. 3 and 4 in that prior art document. When a draw up operation is done with a syringe as described in WO2008057976, at the end of the draw up operation, there is a high likelihood that the flat engagement member will be situated in a position where it is slightly bent upwards resting on a ridge of the grooved surface of the plunger rod. The engagement member of the prior art will thus be biased in the wrong direction. Normally, one click from the engagement member represents a certain dose of the substance in the barrel corresponding to the distance between two adjacent ridges of the grooved surface of the plunger rod. However, the fact that the starting position of the engagement member of WO2008057976 will be one where it is bent slightly upwards, the plunger rod will have to travel much farther than what was initially intended before the first click-sound is generated by the engagement member. The engagement member will in this case have to move first from its position bent slightly upwards towards a position where it is horizontal and thereafter towards a position where it is bent slightly downwards before the first click-sound will be generated. It has been shown that a first dose delivered by such a design may significantly larger than actually intended.

However, due to the inventive allowed relative movement between the plunger and at lea t a portion of the plunger rod, the plunger rod of the syringe according to the first aspect may move a short distance without the plunger moving and consequently without any substance being expelled. Hereby, any additional plunger rod travel required may be allowed without any negative consequences in terms of delivery of a too large initial dose.

Accordingly, at least during an initial portion of the movement after a reversal of movement, the relative movement allows for a compensation of a potential misalignment, incorrect bias or the like in the feedback generating mechanism of a syringe for example according to what has been described in the foregoing. This may, in contrast to the joint movement of the prior art, be described as a separation of the movement of the plunger rod by means of feedback is generated, from the movement of the plunger by means of which the substance in the barrel is delivered, at least during an initial portion of the movement after a reversal of movement.

This compensation with regard to any extra plunger rod travel distance which may arise until a first feedback indication, e.g. a click, is generated by the syringe affects the size of the dose corresponding to the first feedback indication provided after the direction of movement of the plunger rod is reversed. This is due to the fact that the plunger rod may move a predetermined distance before engaging with the plunger to drive the plunger, in other words before any substance is delivered via the needle by means of the plunger moving.

Accordingly, advantages of the invention include that the dosage accuracy is significantly improved, for example with regards to a first dose delivered after a reversal of direction of movement of the plunger rod. In other words, known problems relating to the accuracy of dosage, in particular the accuracy of the first dose administered after the substance has been drawn into the syringe from a vial or the like, are reduced.

The arrangement of the play at the connection of the first and second assembly parts means that, in some embodiments, a gap or play is prevailing in the engagement between the plunger rod and the plunger such that the plunger rod, although arranged to drive the plunger, is further allowed to move a short predetermined distance with respect to, or relative, the plunger. For example, in some embodiments, the allowed predetermined free relative movement is a relative movement such that at least a portion of the plunger rod may move a predetermined distance before engaging the plunger, i.e. without engaging the plunger. In some embodiments, the relative movement is allowed at a predetermined position of at least a portion of the plunger rod, for example with respect to the barrel. In some embodiments, at least a portion of the plunger rod is moving during the relative movement, whereas the plunger may remain still.

Due to the design of the plunger and the plunger rod by means of which the plunger is driven as described in the preceding paragraphs, any additional plunger travel needed before the first feedback, for example after a reversal of the direction of movement of the plunger rod, is generated may thus be performed without expelling (i.e. injecting) any substance. In other words, any additional travel required may be performed independently by the plunger rod while the plunger remains still, i.e. does not move, and consequently while no substance is passed through the needle.

The disclosed syringe is suitable for example for applications wherein the syringe is supplied empty. During use, the substance to be injected is first drawn into the barrel of the syringe for example from a vial. Examples of such substances include botulinum toxin. In certain applications, the substance is then administered to the patient in multiple steps and/or at different injection locations. Due to the design of the syringe feedback is generated each time the substance is injected, each feedback indication normally corresponds to a certain dose of the substance. By dose size should as described above be understood the size of a dose delivered corresponding to one feedback indication, e.g. corresponding to the distance travelled by the plunger rod between two feedback indications. The syringe may in some embodiments be a disposable syringe. Suitable materials for the comprised components include plastics; suitable manufacturing methods include injection moulding. The barrel of the syringe is adapted to contain the substance to be administered. The plunger is movably arranged within said barrel and the plunger rod is provided to drive said plunger, in order to, for example, expel the substance contained in the barrel to be administered through, for example, a cannula attached to the barrel or in some cases draw the substance into the syringe.

The syringe comprises a mechanism for providing feedback to a user as the plunger rod is moved relative the barrel for driving said plunger. The mechanism may for example be adapted to provide an engagement between the plunger rod and the barrel such that feedback is given to a user as the plunger rod is moved relative to the barrel for driving the plunger. In other words, in some embodiments, the plunger rod and barrel may be arranged such that feedback is provided as they move with respect to one another.

In some embodiments, such a mechanism may comprise at least a first element arranged at, or on, the plunger rod and a second element arranged at, or on, the barrel, the first and second element being adapted to form an engagement, and/or to interact as the plunger rod moves with respect to the barrel.

In some embodiments the feedback triggering portion is arranged along the plunger rod. The extension is at least a minor part of the length of the plunger rod, and preferably a major part of its length.

In some embodiments the feedback triggering portion is integrally formed with the plunger rod as a single component, i.e. the feedback triggering portion may constitute, or form, part of the plunger rod. In other embodiments, the feedback triggering portion may be a separate component arranged at the plunger rod. The feedback triggering portion may for example comprise a grooved surface. The feedback generating element is adapted be triggered by the feedback triggering portion, for example by engaging with a grooved surface of the feedback triggering portion, in order to provide feedback to the user as the plunger rod is moved with respect to the barrel. Accordingly, the feedback generating element may in some embodiments be arranged at, or connected to, the barrel. Examples include a resilient arm, or a spring, arranged at the barrel.

One possible form of feedback that may be provided by the mechanism, for example by means of the feedback generating element, and/or by the feedback generating element interacting or engaging with the feedback triggering portion is an audible feedback indication, i.e. a sound such as a click-sound. Other examples include tactile feedback. Such a feedback indication will be repeated when the substance is injected, i.e. as the plunger rod moves with respect to the barrel; each feedback indication commonly correspond to a certain dose of the substance being delivered during injection as described above.

According to one embodiment, the plunger rod comprises first and a second portion such that the second portion is (adapted to be) arranged between the plunger and the first portion and the predetermined relative movement is, or is achieved by means of, a movement between said first portion of said plunger rod and said plunger. In some embodiments, a relative movement between said first and second portion of said plunger rod is allowed. Accordingly, the plunger rod in such embodiments may comprise a first and a second portion and suitable engagement means arranged between said first and second portion, such that a relative movement may be allowed. In some embodiments, the relative movement is allowed upon a reversal of the direction of movement of the plunger rod, such that for example the first portion of the plunger rod following a change, or reversal, of the direction of movement may travel a predetermined distance before engaging the second portion of the plunger rod. In some embodiment, the second portion of the plunger rod is arranged to engage with the plunger in a fixed manner, i.e. the second portion of the plunger rod and the plunger may be fixedly attached.

For example, the first and second portion of the plunger rod may travel in a first direction of movement, the second portion of the plunger rod being fixedly attached to, or engaged with, the plunger. Upon a change of direction of movement to a second, opposite, direction of movement, the first portion may travel an initial predetermined distance before again engaging the second portion of the plunger rod. Accordingly, the second portion of the plunger rod and consequently the plunger will not move during the initial travel of the first plunger rod portion over the predetermined distance, following the reversal of direction of movement. When the first portion of the plunger rod, after the predetermined relative movement has been performed, again engages the second portion of the plunger rod, the plunger rod resumes the driving functionality with respect to the plunger. In one embodiment, the engagement between the first and second portion of the plunger rod is a telescopic arrangement.

According to one embodiment, the predetermined relative movement is, or is achieved by means of, a relative movement between said plunger rod and said plunger. In such an embodiment, the plunger rod may be described as comprising a first portion and a second portion of the plunger rod which are integrally formed, i.e., the plunger rod may be formed as a single, integral or unitary, component. Such an exemplary plunger rod may be arranged to drive the plunger such that a predetermined relative movement between the plunger rod and the plunger is allowed. In other words, a gap (or play) may prevail in the engagement between the plunger rod and the plunger such that the plunger rod although arranged to drive the plunger, is further allowed to move freely a short predetermined distance with respect to the plunger. In one embodiment, the allowed predetermined relative movement is a relative movement such that the plunger rod may move a predetermined distance before engaging the plunger rod. The predetermined relative movement may in some embodiments be allowed in connection with a change of direction of movement of the plunger rod, i.e. the relative movement is allowed when the direction of movement on the plunger rod is reversed.

According to one embodiment, the predetermined relative movement is a predetermined relative movement between said at least one portion of the plunger rod and said plunger wherein at least a portion of the plunger rod and the plunger move independently of one another. For example, the relative movement may be described as a free movement. In one embodiment, the relative movement may further be understood as a movement wherein at least a portion of the plunger rod and the plunger move in of one another, in contrast to the cooperating, or interacting, movement of at least a portion of the plunger rod and plunger yielded when the plunger rod drives the plunger by means of an engagement between the plunger rod and the plunger adapted such that the plunger rod is arranged to drive the plunger. In one embodiment, the predetermined relative movement is a movement wherein at least a portion of the plunger rod may accelerate freely over a predetermined distance with respect to the plunger.

According to one embodiment, the predetermined relative movement is allowed by means of a play between at least a portion of the plunger rod and the plunger. In such an embodiment, the plunger rod and the plunger may for example be arranged with a predetermined play there between. Such a play, or gap, thereby allows for the relative movement due to the design of the engagement. Accordingly, the relative movement or play may be understood as a movement wherein at least the first portion of the plunger rod and the plunger move independently of one another.

According to one embodiment, the predetermined relative movement is allowed by means of a play between the first and the second portion of the plunger rod. I.e. a play is allowed in an engagement between the first and second portion of the plunger rod and the first and second portion of the plunger rod may consequently move independently of one another for example over a predetermine distance.

According to one embodiment, the relative movement is allowed when the direction of movement of the plunger rod is reversed, i.e. the predetermined relative movement is allowed in connection with a change of direction of movement of the plunger rod. Therefore, according to one embodiment, the first and second portion of the plunger rod and the plunger may move jointly in a first direction, the plunger rod driving the plunger. Upon a change of direction of movement of the plunger rod to a second direction of movement, the plunger rod and/or a first portion of the plunger rod may be allowed to move a predetermined distance in the second direction of movement before again engaging, i.e. starting to drive, the plunger and/or the second portion of the plunger nod after the allowed relative movement has been performed. The plunger then moves, i.e. is driven by the plunger rod, in the second direction of movement.

According to one embodiment, the predetermined relative movement may be a movement such that at least the first portion of the plunger rod is allowed to move a predetermined distance d with respect to the plunger upon a reversal of direction of movement of the plunger rod.

According to one embodiment, the plunger is fixedly attached to the second portion of the plunger rod. Alternatively, the plunger and the second portion of the plunger rod may be integrally designed, i.e. formed as a single component.

According to one embodiment, the predetermined relative motion between said at least one portion of the plunger rod and the plunger is allowed irrespective of the direction of movement of the plunger rod prior to the reversal of the direction of movement. According to one embodiment, the play between the plunger and the plunger rod and/or the first and the second portion of the plunger rod prevails independent of the direction of movement of the plunger rod. By direction of movement may for example be understood a direction of movement of the plunger rod prior to a change of direction of movement. Accordingly, the engagement between the plunger rod and the plunger and/or the first and the second portion of the plunger rod may comprise a symmetrical design. Further, according to one embodiment, the predetermined relative motion allowed and/or the play between the plunger rod and the plunger and/or the first and the second portion of the plunger rod comprises substantially the same magnitude in a first direction of movement and in a second direction of movement, i.e., irrespective of the direction of movement of the plunger rod.

According to one embodiment, the plunger rod and the plunger are arranged such that the plunger rod may drive the plunger in a longitudinal direction of the plunger rod. The plunger rod may move along said longitudinal direction. Such an arrangement allows for the plunger to be displaced in the barrel along the longitudinal direction of the plunger rod, in order to for example expel the substance contained in the barrel through the needle during injection.

According to one embodiment, the predetermined relative movement is a predetermined relative movement at least along said longitudinal direction of the plunger rod, i.e. the relative movement between the plunger rod and and at ant a portion of the plunger rod may be allowed in the same direction as the direction of movement of the plunger and/or the plunger rod.

According to one embodiment, at least one of the plunger rod and plunger comprises a mechanism for forming an engagement between the plunger and the plunger rod. Such means may for example be adapted such that the plunger rod may drive the plunger.

According to one embodiment, the plunger comprises a cavity adapted to engage a corresponding structure of the plunger rod. The cavity may for example form part of the mechanism for forming an engagement between the plunger and the plunger rod. Such a cavity is an example of an advantageous space efficient design. According to one embodiment, the plunger is adapted to at least partly surround the plunger rod.

According to one embodiment, the plunger rod comprises a protruding member adapted to engage said cavity of the plunger rod. The protruding member may for example form part of the mechanism for forming an engagement between the plunger and the plunger rod. The shape of the protruding member may correspond substantially to the shape of the cavity mentioned above. In one embodiment, the protruding member is shorter than the extension of the cavity along for example the longitudinal direction of said cavity, such that a relative movement or a play there between may be allowed.

In some embodiments however, the plunger rod comprises a cavity and the plunger a corresponding structure according to what is described in the foregoing paragraphs.

According to one embodiment, at least one of the protruding member of the plunger rod and the cavity of the plunger comprises a tapered shape. In one embodiment, at least one of the protruding member of the plunger rod and the cavity of the plunger comprises an at least partly conical shape. Other examples include a frustum cone-shape. Such a shape may be advantageous for example in that friction between the corresponding structures of the plunger and the plunger rod is reduced during the relative movement.

According to one embodiment, at least one of the first portion and second portion of the plunger rod comprises a cavity adapted to engage a corresponding structure of at least one of the first portion and the second portion of the plunger rod. The cavity may comprise a tapered shape, such as a conical shape or a frustoconical shape.

According to one embodiment, at least one of the first portion and the second portion of the plunger rod comprises a protruding member adapted to engage a cavity of at least one of the first portion and the second portion of the plunger rod. The protruding member may comprise a tapered shape, such as a conical shape or a frustoconical shape.

According to one embodiment, the allowed predetermined relative movement is a relative movement such that the plunger rod may move a predetermined distance, d, before engaging the plunger. According to one embodiment, the allowed predetermined relative movement is a relative movement such that the first portion of the plunger rod may move a predetermined distance, d, before engaging the second portion of the plunger rod. The predetermined relative movement between the first portion of the plunger rod and/or the plunger rod and the plunger may be allowed by means of a gap, in the engagement between said plunger rod and said plunger adapted to allow the plunger rod to drive the plunger and, a predetermined relative movement may be allowed corresponding to the size of the gap in the engagement. In one embodiment, the gap is such that the predetermined relative movement is substantially of the same magnitude irrespective of the direction of movement of the plunger rod.

According to one embodiment, the plunger rod is adapted to drive the plunger in a first direction and a second opposite direction, by means, of the plunger rod exerting a pushing and a pulling force, respectively on the plunger.

According to one embodiment, the first portion of the plunger rod is adapted to drive the second portion of the plunger rod in a first and a second opposite direction, by means of the first portion of the plunger rod exerting a pushing and a pulling force respectively on the second portion of the plunger rod.

According to one embodiment, the first direction of movement is a direction of movement of the plunger rod utilized for filling the syringe by drawing fluid into the syringe. The syringe may be filled for example by drawing fluid from a bottle or vial into the syringe. In one embodiment, the first direction is a direction of movement wherein the plunger rod exerts a pulling force on the plunger. According to one embodiment, the second direction of movement is a direction of movement utilized for performing an injection. In one embodiment, the second direction is a direction of movement wherein the plunger rod exerts a pushing force on the plunger. For example the plunger and plunger rod may move jointly in a first direction, wherein a first surface of the plunger rod may engage a first surface of the plunger, the plunger rod driving the plunger by exerting a pulling force. Upon a change of direction of movement (i.e. a reversal) of the plunger rod to a second direction of movement, the plunger rod is allowed to move a predetermined distance d in the second direction of movement before again engaging, i.e. starting to drive, the plunger after the allowed relative movement d has been performed. The plunger then moves, i.e. is driven by the plunger rod, in the second direction of movement, whereby a second surface of the plunger rod engages a second surface of the plunger, the plunger rod driving the plunger by exerting a pushing force on the plunger. This may for example be the case when an injection is performed. In other words, a gap may prevail between the pair of surfaces of the plunger and the plunger rod adapted to engage when travelling in a first direction, when the plunger and plunger rod move in a second opposite direction and vice versa. The same effect may in some embodiments be achieved by means of an engagement between a first and second portion of the plunger rod, such that a relative movement and hence the exertion of a pushing and pulling force may be allowed between the first and second portion of the plunger rod.

The size of the first dose administered after a change or direct of movement may be designed, or adapted, by means of a combination of the size or magnitude, of the allowed relative movement between the plunger rod and the plunger and/or the first and second portion of the plunger rod. According to one embodiment, the size of the predetermined relative movement is adapted such that a first dose delivered after the change of movement of the plunger rod is smaller than a normal dose. By a normal dose should be understood a dose achieved by means of the plunger rod travelling in one direction, i.e. a first and a second dose delivered subsequently when the plunger rod travels in a first direction of movement between the first and a second dose, in other words a dose delivered when the plunger rod direction of movement is not reversed. According to one embodiment, the size of the predetermined relative movement is adapted such that a first dose delivered after the change of movement of the plunger rod is substantially equal to a normal dose delivered.

According to one embodiment, the feedback triggering portion comprises a grooved surface, wherein the feedback generating element is arranged to engage with said grooved surface of the feedback triggering portion such that feedback is given to a user as the plunger rod is moved relative to the barrel for driving said plunger. In such an embodiment, the grooved surface may comprise ribs, i.e. grooves and/or ridges. The number of grooves, or ridges as well as the distance between the adjacent grooves may be adapted depending on the application. Further, each feedback indication, may correspond to the feedback generating element travelling over one groove of the feedback triggering portion. According to one embodiment, the feedback generating element may comprise an engaging member adapted to engage the grooved surface of the feedback triggering portion. Examples of such an engaging member includes an arm, a resilient arm, a spring element, a ratchet or similar.

According to one embodiment, the size of a first dose delivered after a reversal of the direction of movement of the plunger rod is determined based on a combination of the magnitude of the movement of the plunger rod allowed corresponding to a feedback indication (i.e. the magnitude of the movement of the plunger rod allowed between two consecutive feedback indications provided when the plunger travels in a first direction of movement), and the magnitude of the relative movement allowed upon a reversal of direction of movement of the plunger rod, said at least one portion of the plunger rod being allowed to move a predetermined distance, d, with respect to the plunger upon a reversal of direction of movement of the plunger rod. Hereby the size of the predetermined relative movement may be adapted such that a first dose delivered after the change of movement of the plunger rod is smaller than a normal dose, substantially equal to or larger than a normal dose. By the term normal dose may be understood a dose delivered when the plunger rod direction of movement is not reversed. Such a combination is advantageous in that the size of the first dose achieved after a change of direction of movement may be easily adapted to different applications.

A large distance d compared to the distance travelled by the plunger rod for an intended dose, implying a smaller first dose, may be suitable for application where a large dose must be carefully avoided due to for example serious side effects should a too large dose be delivered. For applications where a larger dose is less serious, a shorter distance d may be chosen compared to the distance travelled by the plunger rod for an intended dose, implying a larger first dose possibly being delivered after a reversal of movement.

For example, in the case of a feedback triggering portion comprising a grooved surface, the distance d may be chosen to be large or small compared to the distance between two ridges of the grooved surface corresponding to an intended dose represented by one feedback indication.

Further, according to one embodiment, the magnitude of the allowed relative movement lies in the interval of 0-5 mm, preferably in the interval of 0.5-2 mm. According to one embodiment, the volume of (the barrel) of the syringe lies in the interval of 0-5 ml, preferably in the interval of 0.25-0.75 ml. According to one embodiment, the inner diameter of (the barrel) of the syringe lies in the interval of 0-5 mm, preferably in the interval of 2-4 mm.

A further embodiment, conceivable within the scope of the claims is an embodiment wherein the syringe further comprises an intermediate member, such that the predetermined relative movement allowed may be a movement between at least a portion of the plunger rod and the intermediate member. Such an intermediate member may for example comprise a cavity adapted to form an engagement with a corresponding structure of said at least one portion of the plunger rod, the engagement allowing for the relative movement. The intermediate member may in some embodiments be fixedly attached to the plunger and/or the second portion of the plunger rod.

According to a second aspect of the invention a plunger assembly for a syringe is provided, said assembly comprising a plunger, and a plunger rod adapted to drive said plunger, wherein the plunger rod is arranged to drive said plunger such that a predetermined relative movement between at least a portion of the plunger rod and the plunger is allowed.

Further objectives of, features of and advantages with the present invention will become apparent when studying the following detailed disclosure, the drawings and the appended claims. Those skilled in the art realize that different features of the present invention can be combined to create embodiments other than those described in the following.

BRIEF DESCRIPTION OF THE DRAWINGS

The invention will be better understood through the following illustrative and non-limiting detailed description of preferred embodiments, with reference to the appended drawings, in which.

All figures are schematic, not necessarily to scale, and generally only show parts which are necessary in order to elucidate the invention, wherein other parts may be omitted or merely suggested.

DETAILED DESCRIPTION OF EMBODIMENTS

Figure 1:
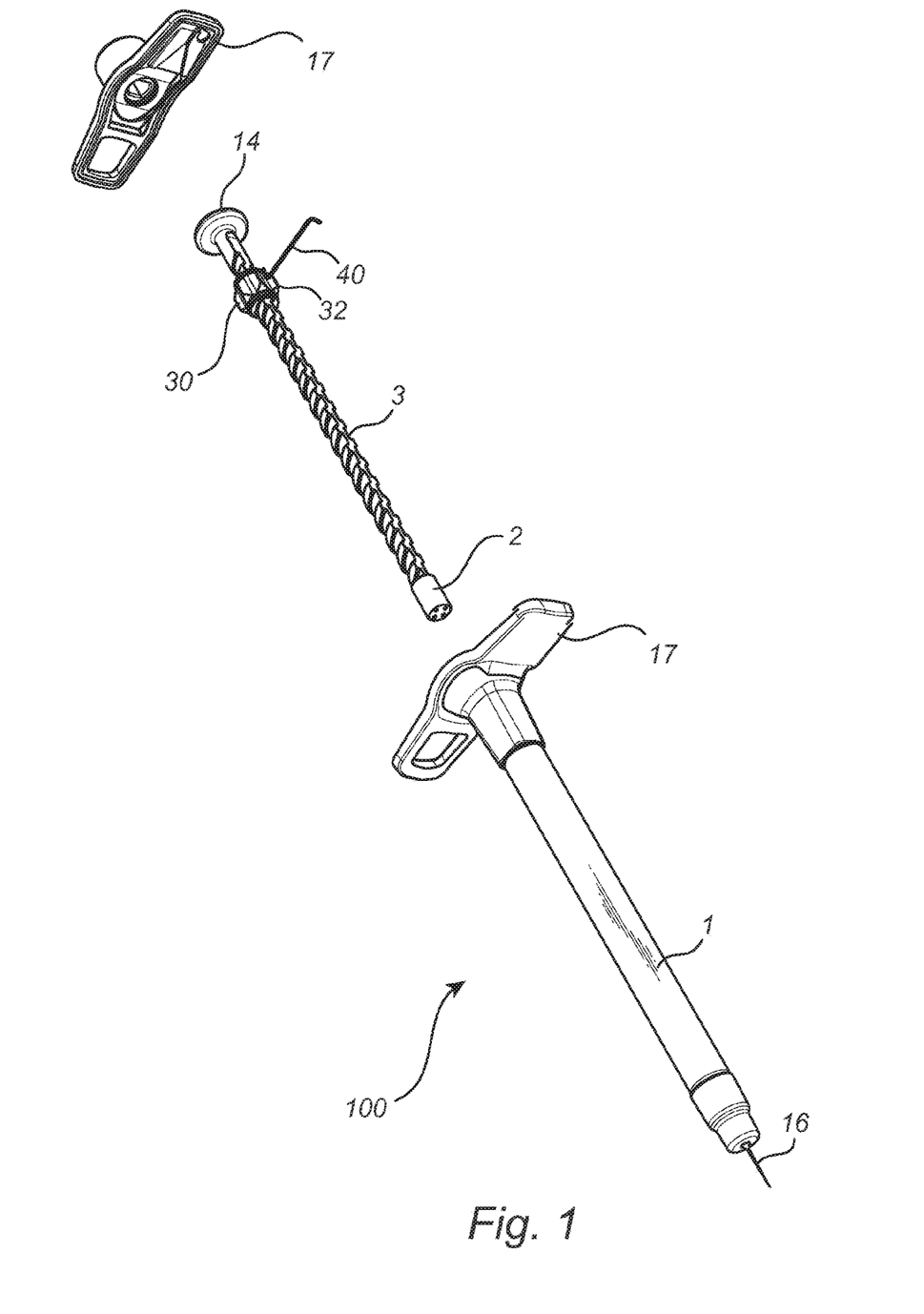
FIG. 1 is a perspective view of a syringe according to one embodiment of the invention.

An exemplary syringe 100 according to an embodiment of the invention is shown in FIG. 1. The syringe comprises a barrel 1, and a plunger assembly comprising a plunger 2 movably arranged within the barrel 1 and a threaded plunger rod 3 for driving the plunger 2. The plunger rod 3 is further provided with a thumb plate 14 for activation of the plunger rod 3 and at least one flat surface. The plunger rod 3 is adapted to drive the plunger 2, i.e. to engage the plunger 2 such that the plunger 2 may preferably be moved in both directions though the barrel, and further such that a predetermined free relative movement is allowed between a first assembly part, and a second assembly part. The first assembly part consists of at least a portion of the plunger rod 3, and the second assembly pert consists of at least the plunger 2. The first and second assembly parts are connected with a play, which provides for the free relative movement, as will be described in more detail below with reference to FIGS. 3a, 3b, 4a, and 4b. The syringe 100 further comprises a needle 16. The barrel may be provided with a finger grip 17 having a through-hole with at least one flat surface matching the flat surface of the plunger rod, which through-hole is configured to engage and to guide the plunger rod such that it does not rotate relative to the barrel.

The syringe 100 further comprises a mechanism for providing feedback to a user as the plunger rod 3 is moved relative to the barrel 1 for driving said plunger, in the illustrated case in the form of a feedback triggering portion 30 and a feedback generating element 40. The feedback triggering portion 30 of the illustrated embodiment is arranged at the plunger rod 3 and has a substantially circular or annular shape, i.e. may be described as having a wheel shape. Further the feedback triggering portion comprises a grooved surface 32 comprising a plurality of ribs, i.e. alternating ridges, or protrusions, and grooves, or valleys, provided in an alternating manner along the surface 32. The grooved surface 32, and consequently the plurality of grooves and ridges, is/are provided along the circumference of the feedback triggering portion. The feedback generating element 40 is arranged at an upper end of the barrel 1 to engage with the grooved surface 32 of the feedback triggering portion 30, thereby being triggered by the feedback triggering portion such that feedback is given to a user as the plunger rod 3 is moved relative to the barrel for driving the plunger 2. The feedback triggering portion 30 rotates relative to the barrel and relative to the feedback generating element 40, while the plunger rod moves axially, rotationally locked relative to the barrel.

Figure 2:
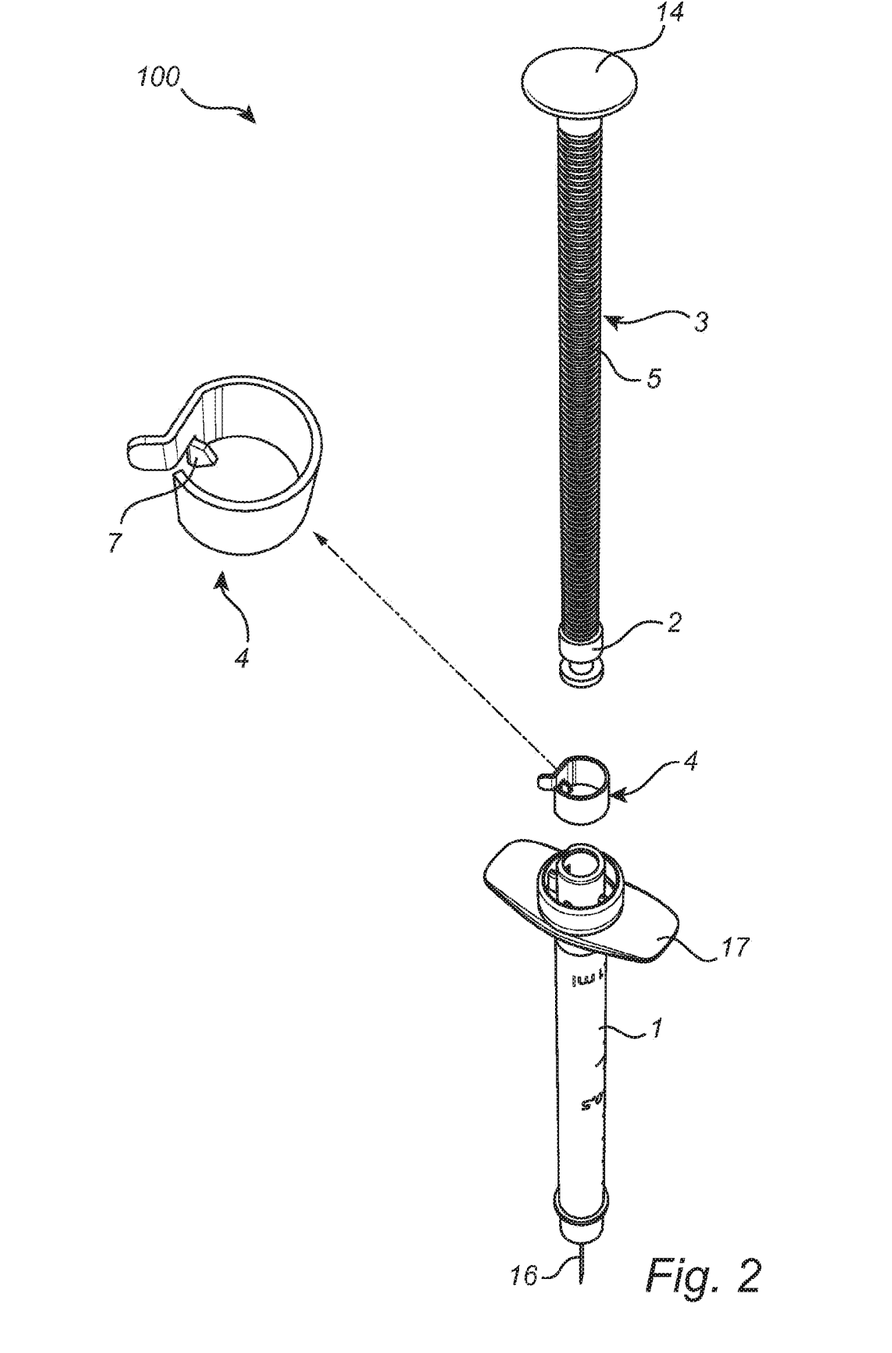
FIG. 2 is perspective view of a syringe according to another embodiment of the invention.

Another exemplary embodiment of the syringe 100, shown in FIG. 2, comprises a barrel 1, and a plunger assembly comprising a plunger 2 and a plunger rod 3 arranged to drive the plunger 2 during use of the syringe 100 and provided with a thumb plate 14 for activation of the plunger rod 3. The syringe 100 further comprises a needle 16 and the barrel 1 can be provided with a finger grip 17.

The embodiment of the syringe illustrated in FIG. 2 also comprises a mechanism for providing feedback to a user as the plunger rod 3 is moved relative to the barrel 1 for driving said plunger which may be described as a feedback triggering portion and a feedback generating element. In this case, the plunger rod 3 is provided with a grooved outer surface, which may be described as the feedback triggering portion, in this case integrally formed with/forming part of the plunger rod, which is arranged to drive the plunger such that a predetermined free relative movement may be allowed between at least a portion of the plunger rod 3 and the plunger 2. The syringe 100 further comprises a feedback generating element 4 arranged at the barrel, comprising a generally radially inwardly protruding element 7 arranged to engage the grooved surface 5 of the plunger rod 3 such that feedback is provided to the user as the plunger rod moves axially with respect to the barrel and with respect to the generally radially inwardly protruding element 7.

In both disclosed embodiments, the engagement between the respective feedback triggering portion and feedback generating element and the grooved surfaces is such that feedback to the user in the form of a click-sound, and possibly also in the form of a tactile feedback, is generated as the feedback generating element move over the ribs and grooves of the grooved surfaces.

In common with all embodiments of this patent application, the plunger rod 3 illustrated in FIGS. 1 and 2 respectively is arranged to drive the plunger 2 such that a predetermined free relative movement between the first assembly part constituted by at least a portion of said plunger rod, and the second assembly part constituted by at least the plunger is allowed (not shown in FIGS. 1 and 2). Exemplary embodiments of the connection between the first and second assembly parts, such as the engagement between the plunger rod and the plunger, will be described in the following.

Figure 3A:
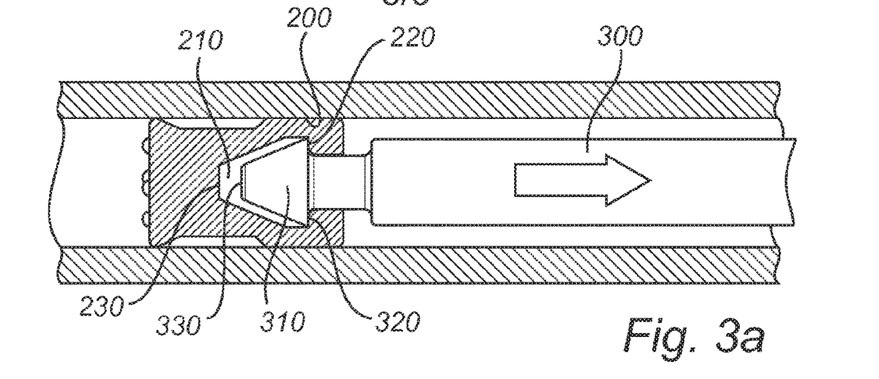
FIG. 3a is a cross-sectional view of a detail of a plunger and plunger rod of a syringe according to one embodiment arranged in a first position.
Figure 3B:
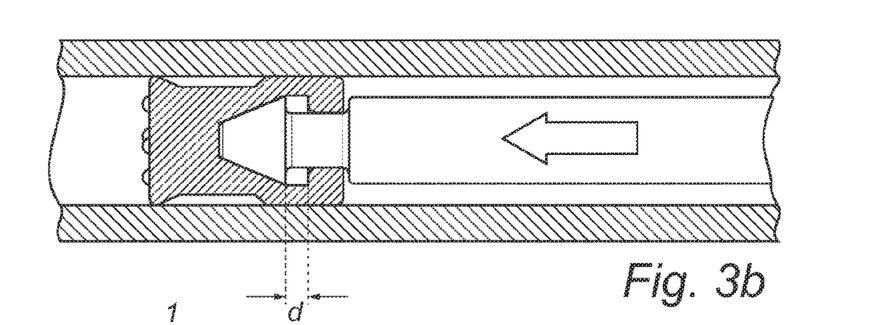
FIG. 3b is a cross-sectional view of a detail of a plunger and plunger rod of the syringe of FIG. 3a arranged in a second position.

FIGS. 3a and b show a detailed view of the engagement between a plunger 200, constituting the first assembly part, and a plunger rod 300, constituting the second assembly part, of an embodiment of the syringe, whereby the plunger rod 300 is arranged to drive the plunger 200 such that a predetermined relative movement said plunger rod 300 and said plunger 200 is allowed. In the illustrated embodiment in FIGS. 3a and b, the allowed predetermined relative movement is a predetermined relative movement between the plunger rod and the plunger wherein the plunger rod and the plunger may move independently of one another. In practice, the plunger rod 300 commonly moves while the plunger 200 remains still during the relative movement. In other words, a play prevails between the plunger rod and said plunger such that the plunger rod 300 may move a predetermined distance d before engaging the plunger 200. This relative movement is for example allowed in connection with a change of direction of movement of the plunger rod 300, i.e. the relative movement is allowed when the direction of movement on the plunger rod 300 is reversed, for example before the initial dose is delivered after drawing of a substance into the syringe.

In the illustrated embodiment the plunger rod 300 and the plunger 200 are arranged such that the plunger rod 300 may drive the plunger 200 in a longitudinal direction of the plunger rod 300. The plunger rod 300 may further drive the plunger 200 in a first and a second opposite direction by means of the plunger rod 300 exerting a pushing and a pulling force respectively on the plunger. The predetermined relative motion between the plunger rod 300 and the plunger 200 is allowed independent of the direction of movement of the plunger rod 300.

In order to provide the engagement between the plunger 200 and the plunger rod 300 the plunger 200 comprises a cavity 210 adapted to engage a corresponding structure of the plunger rod 300. The cavity has a tapered shape, in the illustrated embodiment that of a frustum cone comprising a first surface 220 and a second surface 230. The plunger rod 300 comprises a protruding member 310 adapted to engage the cavity 210 of the plunger 200. The protruding member 310 has a shape corresponding to that of the cavity, i.e. a tapered shape, in the illustrated embodiment that of a frustum cone, and comprises a first surface 320 and a second surface 330.

With regard to the functionality of the engagement, the plunger and plunger rod may move jointly in a first direction, illustrated in FIG. 3a showing the plunger and plunger rod when moving in the direction of the arrow. The first surface 320 of the plunger rod engages the first surface 220 of the plunger 200, the plunger rigid 300 driving the plunger 200 by exerting a pulling force. This may for example be the case when drawing a substance from a vial into the syringe. Upon a change of direction of movement (i.e. a reversal) of the plunger rod 300 to a second direction of movement, illustrated in FIG. 3b, the plunger rod 300 is allowed to move a predetermined distance d in the second direction of movement (indicated by the arrow in FIG. 3b) before again engaging, i.e. starting to drive, the plunger 200 after the allowed relative movement has been performed. The plunger 200 then moves, i.e. is driven by e plunger rod 300, in the second direction of movement, whereby the second surface 330 of the plunger rod 300 engages the second surface 230 of the plunger 200, the plunger rod 300 exerting a pushing force on the plunger 200. This may for example be the case when an injection is performed. In other words, a gap prevails between the pair of surfaces of the plunger 200 end the plunger rod 300 adapted to engage when travelling in a first direction, when the plunger and plunger rod move in a second opposite direction and vice versa. The plunger rod 300 may therefore, although arranged to drive the plunger, be allowed to move freely a short predetermined distance d with respect to the plunger 200 upon a reversal of the direction of movement.

Figure 4A:
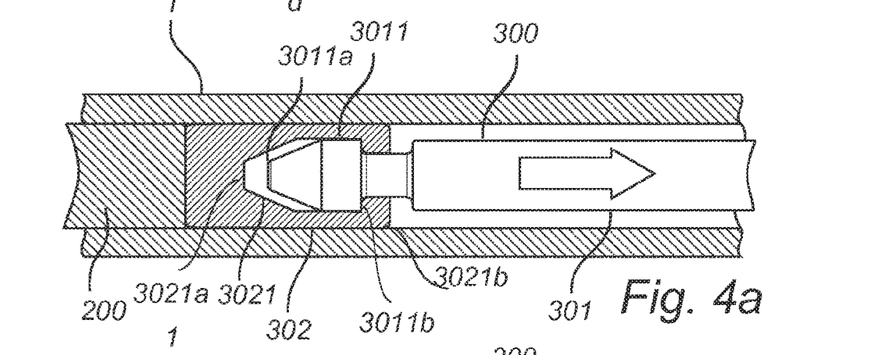
FIG. 4a is a cross-sectional view of a detail of a plunger and plunger rod of a syringe according to one embodiment arranged in a first position.
Figure 4B:
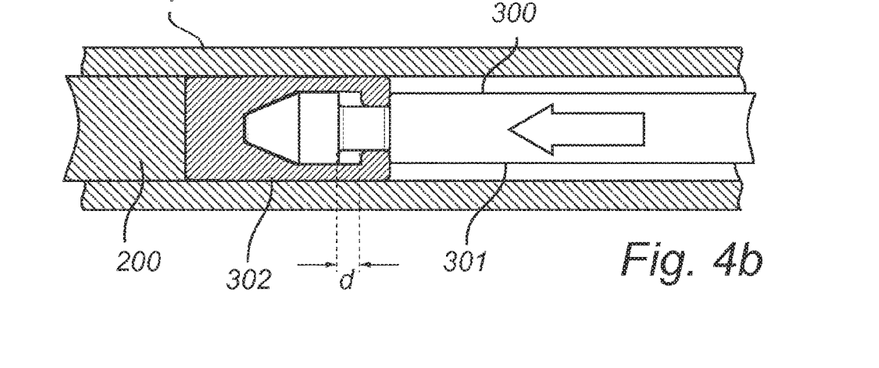
FIG. 4b is a cross-sectional view of a detail of a plunger and plunger rod of the syringe of FIG. 4a according to one embodiment arranged in a second position.

FIGS. 4a and 4b show a detailed view of another exemplary embodiment of the connection between the first and second assembly parts, as an engagement between a plunger 200 and a plunger rod 300 of an embodiment of the syringe, whereby the plunger rod 300 is arranged to drive the plunger 200 such that the predetermined free relative movement between the plunger rod and the plunger is a relative movement between a portion 301 of the plunger rod 300 the plunger 200. In the illustrated embodiment in FIGS. 4a and b, the allowed predetermined relative movement is a predetermined relative movement wherein the first portion 301 of plunger rod 300 and the plunger move independently of one another, i.e. the first portion 301 of the plunger rod may move independently of the plunger 200. Further, the relative movement is a relative movement between the first and second portion of the plunger rod 301, 302. This means that in this embodiment the first assembly part is constituted by the first portion of the plunger rod 301, and the second assembly part is constituted by the plunger 200 and the second portion 302 of the plunger rod.

In other words, a play prevails between the first and second portion of the plunger rod 301, 302 such that the first portion of the plunger rod 301 may move a predetermined distance d independently, i.e. not driving the plunger 200. This relative movement is for example allowed in connection with a change of direction of movement of the first portion of the plunger rod 301, i.e. the relative movement in allowed when the direction of movement on the first portion of the plunger rod 301 is reversed.

The plunger rod of the illustrated embodiment comprises a first and a second portion 301, 302 wherein the second portion of the plunger rod 302 is fixedly attached to the plunger 2. Suitable attachment means include for example a threaded connection. Alternatively, the plunger and the second portion of the plunger rod may be integrally designed, i.e. formed as a one single component.

Further, in the illustrated embodiment, the plunger rod 300 and the plunger 200 are arranged such that the plunger rod 300 may drive the plunger 200 in a longitudinal direction of the plunger rod 300. The plunger rod 300 may further drive the plunger 200 in a first and a second opposite direction by means of the plunger rod 300 exerting a pushing and a pulling force respectively on the plunger. The predetermined relative motion between the plunger rod 300 and the plunger 200 is allowed independent of the direction of movement of the plunger rod 300.

In order to provide the engagement between the first portion of the plunger 301 and the second portion of the plunger rod 302, the second portion of the plunger rod 302 comprises a cavity 3021 adapted to engage a corresponding structure of the first portion of the plunger rod 301. The cavity 3021 has a tapered shape, in the illustrated case that of a frustum cone comprising a first surface 3021a and a second surface 3021b. The first portion of the plunger rod 301 comprises a protruding member 3011 adapted to engage the cavity 3021 of the second portion of the plunger rod 302. The protruding member 3011 has a shape corresponding to that of the cavity 3021, i.e. a tapered shape, in the illustrated that of a (frustum) cone, and comprises a first surface 3011a and a second surface 3011b.

The first and second portions of the plunger rod 301, 302 (and consequently the plunger) may move jointly in a first direction, illustrated in FIG. 4a showing the first and second portion of the plunger rod 301, 302 and the plunger 200 when moving in the direction of the arrow. The plunger 200 is fixedly attached to the second portion of the plunger rod and accordingly moved with the second portion of the plunger rod. The first surface 3011a of the first portion of the plunger rod engages the first surface 3021a of the second portion of the plunger rod, the first portion of the plunger rod 300 driving the second portion of the plunger rod by exerting a pulling force. This may for example be the case when drawing a substance from a vial into the syringe. Upon a change of direction of movement (i.e. a reversal) of the plunger rod 300 to a second direction of movement, illustrated in FIG. 4b, the first portion of the plunger rod 300 is allowed to move a predetermined distance d in the second direction of movement (indicated by the arrow in FIG. 4b) before again engaging, i.e. starting to drive, the second portion of the plunger rod after the allowed relative movement has been performed. The second portion of the plunger rod then moves, i.e. is driven by the first portion of the plunger rod 300, in the second direction of movement, whereby the second surface 3011b of the first portion of the plunger rod 300 engages the second surface 3021a of the second portion of the plunger rod, the first portion of the plunger rod 300 exerting a pushing force on the second portion of the plunger rod. This may for example be the case when an injection is performed.

A further embodiment (not shown), conceivable within the scope of the claims is an embodiment wherein the syringe further comprises an intermediate member, such that the predetermined relative movement may be a movement between at least a portion of the plunger rod and the intermediate member. Such an intermediate member may for example comprise a cavity adapted to form an engagement with a corresponding structure of the first portion of the plunger rod allowing for the relative movement according to what has been described above. The intermediate member may be fixedly attached to the plunger.

Common to all embodiments is that by means of an arrangement as described above allowing a relative movement which may be referred to as a "plunger slack", an advantageous improved control of for example the size of the first dose delivered following a change of direction of the plunger rod is achieved, regardless of the mechanism employed for providing feedback to the user corresponding to delivery of a dose. This is due to the design allowing for a compensation, or compensating effect, of a potential small extra plunger rod travel distance which may arise until a first feedback, e.g. a click, is generated by a mechanism such as for example the mechanism disclosed above when the direction of movement of the plunger rod is changed, i.e. reversed.

Such a combination, i.e. a combination of the plunger slack mechanism and a mechanism allowing for feedback to the user, is further advantageous in that the size of the first dose achieved after a change of direction of movement may be designed, or adapted, by means of a combination of the size, or magnitude, of the magnitude of the movement of the plunger rod allowed corresponding to one feedback indication (e.g. a click), and the design of the size, or magnitude, of the allowed relative movement d between the plunger rod and the plunger, i.e. the plunger slack. Hereby the size of the predetermined relative movement may be adapted such that a first dose delivered after the change of movement of the plunger rod is smaller than normal dose, substantially equal to or larger than a normal dose. By the term normal dose may be understood a dose delivered when the plunger rod direction of movement is not reversed.

While the invention has been illustrated and described in detail in the drawings and foregoing description, such illustration and description are to be considered illustrative or exemplary and not restrictive; the invention is not limited to the disclosed embodiments. The skilled person understands that many modifications, variations and alterations are conceivable within the scope as defined in the appended claims.

Additionally, variations to the disclosed embodiments can be understood and effected by those skilled in the art in practicing the claimed invention, from a study of the drawings, the disclosure, and the appended claims, the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the claims.

The invention claimed is:

1. A syringe comprising a barrel, a plunger assembly comprising a plunger moveably arranged within said barrel and a plunger rod for driving said plunger, and a feedback triggering portion and a feedback generator structured to provide at least audible feedback to a user as the plunger rod is moved relative to the barrel for driving said plunger, the feedback triggering portion arranged at an outer surface of the plunger rod and extending along the plunger rod, and the feedback generator arranged at the barrel, and arranged to generate feedback by being triggered by the feedback triggering portion during movement of the plunger rod relative to the barrel, wherein the plunger assembly comprises a first assembly part comprising at least a part of the plunger rod, and a second assembly part comprising at least the plunger, and a connection portion where the first assembly part and the second assembly part are connected with a gap providing a play such that a predetermined free relative movement is permitted between the first assembly part and the second assembly part within a predetermined distance in a longitudinal direction of the plunger rod prior to engagement of a distal surface of a first portion of the plunger rod and a proximal surface of a second portion of the plunger rod, wherein said second portion is arranged between said plunger and said first portion, and wherein said first assembly part comprises said first portion, and said second assembly part comprises said second portion and said plunger.

2. The syringe according to claim 1, wherein said predetermined free relative movement is a movement between said plunger rod and said plunger.

3. The syringe according to claim 1, wherein the predetermined free relative movement is allowed when the direction of movement of the plunger rod is reversed.

4. The syringe according to claim 3, wherein the predetermined free relative movement is a movement such that said first assembly part is allowed to move the predetermined distance with respect to the second assembly part upon a reversal of direction of movement of the plunger rod.

5. The syringe according to claim 3, wherein the predetermined free relative motion between the first assembly part and the second assembly part is allowed irrespective of the direction of movement of the plunger rod prior to a reversal of the direction of movement.

6. The syringe according to claim 1, wherein at least one of the plunger rod and the plunger comprises grooves disposed between the plunger and the plunger rod.

7. The syringe according to claim 6, wherein the plunger rod comprises a protrusion, the protrusion having a tip dimensioned to be received by a cavity of the plunger rod.

8. The syringe according to claim 1, wherein the plunger rod is adapted to drive the plunger in a first direction and in a second direction opposite to the first direction, by the plunger rod exerting a pushing force and a pulling force respectively on the plunger.

9. The syringe according to claim 1, wherein the size of a first dose delivered after a reversal of the direction of movement of the plunger rod is determined based on a combination of:

the magnitude of the movement of the plunger rod allowed between two consecutive feedback indications provided when the plunger travels in a first direction of movement, and the magnitude of the relative movement allowed upon the reversal of direction of movement of the plunger rod, at least one portion of the plunger rod being allowed to move the predetermined distance with respect to the plunger upon the reversal of direction of movement of the plunger rod.

10. The syringe of claim 1, wherein the relative movement allows for compensation of misalignment or bias of the feedback generator.

11. A syringe comprising: a barrel; a plunger assembly comprising a plunger moveably arranged within said barrel and a plunger rod for driving said plunger; and a feedback triggering portion and a feedback generator structured to provide at least audible feedback to a user as the plunger rod is moved relative to the barrel for driving said plunger, the feedback triggering portion arranged at an outer surface of the plunger rod and extending along the plunger rod, and the feedback generator arranged at the barrel, and arranged to generate feedback by being triggered by the feedback triggering portion during movement of the plunger rod relative to the barrel, including movement while substance contained in the barrel is expelled from the barrel, wherein the plunger assembly comprises a first assembly part comprising at least a part of the plunger rod, and a second assembly part comprising of at least the plunger, and a connection portion where the first assembly part and second assembly part are connected with a gap providing a play such that a predetermined free relative movement is permitted between the first assembly part and the second assembly part within a predetermined distance in a longitudinal direction of the plunger rod prior to engagement of a distal surface of a first portion of the plunger rod and a proximal surface of a second portion of the proximal rod, wherein said second portion is arranged between said plunger and said first portion, and wherein said first assembly part comprises said first portion, and said second assembly part comprises said second portion and said plunger.

* * * * *